United States Patent [19]

McMichael

[11] Patent Number: 4,702,911
[45] Date of Patent: Oct. 27, 1987

[54] PREPARATION OF BACTERIUM PILI SUBUNITS AND VACCINES CONTAINING PILI SUBUNITS

[75] Inventor: John C. McMichael, Tampa, Fla.

[73] Assignee: ImmunoMed Corporation, Tampa, Fla.

[21] Appl. No.: 895,588

[22] Filed: Aug. 14, 1986

Related U.S. Application Data

[63] Continuation of Ser. No. 781,065, Sep. 27, 1985, abandoned, which is a continuation-in-part of Ser. No. 571,347, Jan. 16, 1984, abandoned.

[51] Int. Cl.$^4$ .................. A61K 39/108; A61K 39/02; A61K 39/116; C07K 3/28
[52] U.S. Cl. ..................................... 424/92; 530/418; 530/420; 530/825
[58] Field of Search .................. 424/92; 530/825, 418, 530/420

[56] References Cited

U.S. PATENT DOCUMENTS 4,237,115 12/1980 Brinton, Jr. .......................... 424/92
4,298,597 11/1981 Acres et al. .......................... 424/92
4,454,116 6/1984 Brinton, Jr. .......................... 424/92
4,472,302 9/1984 Karkhanis .......................... 424/92 X

OTHER PUBLICATIONS

J. of Bacteriology, 138, No. 3 (1979), 969–975, McMichael et al.
FEMS Microbiology Letters, 12 (1981), 229–232, Isaacson et al.
Annals of Clinical Research, 14 (1982), 272–277, Korhonen et al.

Primary Examiner—Howard E. Schain
Attorney, Agent, or Firm—Pettis & McDonald

[57] ABSTRACT

A method for obtaining bacterium pili subunits directly from specified bacteria is disclosed and claimed. Dependent upon the bacterium from which the pili subunits are to be obtained, the pH of extraction solutions will be adjusted accordingly. Pili subunits obtained in accord with the method of this invention are useful for preparing vaccines which exhibit good protection against heterologous strain infections.

22 Claims, No Drawings

PREPARATION OF BACTERIUM PILI SUBUNITS AND VACCINES CONTAINING PILI SUBUNITS

This is a continuation of application Ser. No. 781,065, filed 9/27/85 which is a continuation of Ser. No. 06/571,347, filed 1/16/84, both now abandoned.

BACKGROUND OF THE INVENTION

1. Field of the Invention

The present invention relates to a unique method for obtaining bacterium pili subunits suitable for use in preparing a vaccine.

2. Description of the Prior Art

Pili, also referred to as fimbriae, are hairlike organelles attached to the outer surface of bacteria. Pili are composed of many identical protein subunits arranged in a helical array. For pathogenic bacteria, pili are important for virulence, and their role appears to be that of promoting adherence of the bacterium to the host's tissues. That is to say, the importance of pili lies in the fact that they participate in the pathogenic process of many disease causing bacteria. The first step in any bacterial infection is attachment of the bacteria to the host's tissues. The second step is the colonization phase during which the bacteria divide and increase their numbers at or near the site of initial attachment. The third step is the actual pathogenic step which can vary from one bacterial species to the next. For example, in the case of enterotoxogenic *E. coli*, toxins are secreted by the bacteria which damage host tissue and cause fluids to move into the gut resulting in diarrhea.

As revealed in the prior art patents and professional publications, several vaccines have already been developed and are being developed utilizing pili as immunogens. Because pili are important in the early adhesion stages of infections, these vaccines are thought to act to prevent the subsequent colonization step and, thereby, to subvert the infection. Literally all known vaccines today contain intact pili.

The strains of bacteria used to prepare such vaccines are selected on the basis of pilus serotype. In the case of *N. gonorrhoeae* bacteria, the serotype of these pili is highly variable. Therefore, great care must be used in the selection of the strains selected to produce the vaccine to obtain the broadest range of protection. There is a low level of cross reactivity among the pili produced by the different strains, but compared to the antigenicity of the variable portions of the pili subunit, this is minor. Thus, although such an "intact pilus" vaccine gives good protection against infection with the homologous strain of bacteria, it gives much poorer protection against heterologous strains.

Exemplar prior art patent teachings concerned with vaccines utilizing a pili component are Brinton's U.S. Pat. No. 4,237,115 and U.S. Pat. No. 4,298,597 to Acres. Both these patents disclose vaccines of an "intact pilus" type. Othe analogous prior art disclosures are contained in the following U.S. Pat. Nos.:

Homma, U.S. Pat. No. 3,928,565
Fullerton, U.S. Pat. No. 4,199,565
Buchanan, U.S. Pat. No. 4,203,971
Karkhanis, U.S. Pat. No. 4,220,638
Helting, U.S. Pat. No. 4,271,147.

Just as a study of prior patent literature reveals pertinent disclosures, so also does a review of prior professional literature. For example, this inventor recognized that pili might be further degraded into subunits in his paper titled, "Isolation of and Some Physical-Chemical Properties of Pili Isolated from Type 2 Colonies of *Neisseria gonorrhoeae*," which appeared in *PILI*, D. E. Bradley, Ed., International Conferences on Pili, Washington, D.C. 1978. Further pertinent prior art disclosure has also been made by this inventor in his article titled, "Structure of Common Pili from *Escherichia coli*," JOURNAL OF BACTERIOLOGY, Vol. 138, No. 3, June 1979 at 969-975. In the second article, this inventor discusses not only a method for obtaining pili, but also means for disrupting purified pili into subunits, or pilin. Isaacson, et al, in their article titled, "*Escherichia coli* K99 Pili Are Composed of One Subunit Species," FEMS MICROBIOLOGY LETTERS, 12 at 229-232 (1981), confirm the work of this inventor as reported by him in Volume 138 of the JOURNAL OF BACTERIOLOGY, and present further findings concerning the structure of K99 subunits. More recently, Korhonen and Rhen, in their article titled, "Bacterial Fimbriae as Vaccines," ANNALS OF CLINICAL RESEARCH, Vol. 14 at 272-277 (1982), have recognized the limitations of "intact pilus" vaccines and have recognized that a subunit vaccine would probably exhibit greater efficacy against heterologous strains.

Thus, it is clear that vaccines prepared from intact, or whole, pili are well known in the prior art. It is also accurate to state that the prior art has recognized the hypothetical desirability of preparing pili subunit vaccine. It is postulated that in such a subunit vaccine, the antigenic zones (epitopes) which are identical for the pili from one strain to the next would be exposed. Accordingly, such a subunit vaccine would permit a greater degree of cross protection against different bacterial strains.

The primary difficulties associated with producing a pili subunit vaccine have basically involved determining a commercially-acceptable procedure for deriving the pili subunits so that a subunit vaccine can be readily prepared in accord with accepted manufacturing processes.

SUMMARY OF THE INVENTION

The present invention relates to a unique method for harvesting pili subunits, or pilin, directly from bacteria in a liquid suspension. Pili subunits thus obtained are extremely useful in preparing vaccines which exhibit increased cross protection against different bacterial strains. To understand the advantage of the pili subunits and vaccines containing pili subunits, one must have some understanding of the structure and function of pili. A pilus subunit expresses both hypervariable and constant regions. The hypervariable region is on the outer surface of the intact structure, and it is this region that causes the wide range in serotype. The advantage from the bacterium's point of view is that the host, once immunized against one strain of the bacteria can be reinfected by a different strain. This may significantly explain the high rate of recidivism observed in venereal disease clinics. Preparation and use of pili subunits in accord with this invention actually maximizes the constant region of a pilus subunit. These constant regions are essentially the same regardless of the bacterial strain, and are important for at least two pili functions. One of these functions is to confer the basic structure to the intact pilus. The other confers biological activity. Rationale for using pili subunits is that in this form of the antigen, more of the constant regions of the subunit are exposed, and a stronger antibody response toward those sites can be expected. Since a constant region is found in pili of one class from related species a greater degree of cross-reactivity derives from their use. Furthermore, since these constant regions are responsible for the biological activity of the pili, that is, adherence to the host's tissue, antibodies directed to such sites should be more effective in ameliorating the infection.

As a direct result of experimental work conducted by this inventor utilizing the procedures and methods set forth in greater detail hereinafter, pili subunits have been obtained from *Neisseria gonorrhoeae, Moraxella bovis,* and *Escherichia coli* bacteria. With specific regard to the *E. coli,* subunits of type 1 pili were obtained. In all cases, the pili subunits were harvested directly from their bacteria in liquid suspension according to a relatively simple, economical and yet efficient method. Vaccines prepared from the *N. gonorrhoeae* pili have demonstrated efficacy against gonorrhea, and it is anticipated, as a result of this inventor's work, that a vaccine prepared from subunits will demonstrate similar efficacy against a broader range of gonorrhea infections. Vaccines prepared from *M. bovis* pili have demonstrated efficacy against infectious bovine keratoconjunctivitis, and it is similarly anticipated that subunit vaccines will have a broader range of efficacy. *E. coli* strains causing scours in cattle, diarrhea in pigs, and urinary infections in humans have pili closely related to type 1 pili. Thus, a pili subunit vaccine could be prepared against all these infections.

As a result of this inventor's work to date, it seems clear that pili subunits can be obtained from and subunit vaccines can be developed against, virtually any piliated pathogenic bacteria. For example, pili subunits may be obtained from *Neisseria meningitidis* in accord with the method utilized for obtaining pili subunits for *N. gonorrhoeae* and Moraxella specie. It is believed that essentially the same method may be utilized to obtain pili subunits from *Pseudomonas aeruginosa.* Pili subunits can be obtained directly from Salmonella specie and Shigella specie according to a method substantially similar to that followed in obtaining *E. coli* type 1 pili subunits. It is accordingly believed that similar pili subunits may be obtained, and subunit vaccines prepared, from many of the following piliated pathogenic bacteria:

| GRAM NEGATIVE | GRAM POSITIVE |
|---|---|
| *Klebsiella pneumoniae* | *Corynebacterium diptheriae* |
| Proteus specie | *Corynebacterium renale* |
| *Vibrio cholerae* | Actinomyces specie |
| Aeromonas specie | *Fusobacterium necrophorum* |
| *Bordetella pertussis* | *Streptococcus pyogenes* |
| *Bacteroides nodosus* | *Streptococcus sanguis* |
| *Legionella pneumophila* | *Propionibacterium acnes* |
| *Pasteurella multocida* | *Bacillus cereus* (spores) |
| *Yersinia enterocolitica* | *Moraxella bovis* |
| Acinetobacter specie | |
| Providencia specie | |

In all cases, once the pili subunits have been obtained, the corresponding pili subunit vaccine is prepared in accord with normal technology and procedures. Accordingly, subunit vaccines prepared in accord with this invention would consist essentially of a normal saline or buffer solution containing the pili subunits and an appropriate adjuvant.

Two basic methods for obtaining pili subunits in accord with the scope of this invention have been determined and are set forth in greater detail hereinafter. However, both methods are quite similar in that they both provide means for obtaining, or harvesting, the pili subunits directly from their bacteria in liquid suspension. It has been determined that, dependent upon the bacterium from which the pili subunits will be obtained, controlled adjustment of the pH of liquid suspension phases will result not only in separation of the intact pili from their bacteria, but also in disruption of the separated pili into the desired pili subunits. In all cases, the initial step of the method of this invention involves growth of the selected bacteria in accord with standard procedures. The bacteria are then harvested directly into virtually any neutral buffer solution. For example, N-tris (hydroxymethyl) methyl-2-aminoethane sulfonic acid (TES) may be used to prepared a buffer adjusted to pH 6-8, and preferably pH 7.0, with sodium hydroxide. This TES buffer has proved to be quite suitable for harvesting the bacteria. Then, for *N. gonorrhoeae, N. meningitidis* and Moraxella specie, the pH of the solution is raised to about pH 9-11 and agitated to disrupt the pili from the bacteria. This solution is centrifuged and the resulting pellet is discarded, retaining the pili-containing supernatant. The pili-containing supernatant is then adjusted so that its pH is raised to above pH 11.25 resulting in disruption of the pili into subunits. The pili subunits are caused to separate from the high pH solution, and subsequent centrifugation results in the formation of a pili subunit pellet which is suitable for use in preparing a pili subunit vaccine. In the case of *E. coli,* Salmonella specie, and Shigella specie bacteria, a slight modification of the method is necessary in order to separate the pili and disrupt them into the desired subunits. Following initial harvesting of the bacteria in the TES buffer solution, the pH is adjusted to below pH 2, and preferably about pH 1.8, by the addition of hydrogen chloride. This low pH solution is then placed into a boiling water bath for about five minutes resulting in the disruption of the intact pili. After removal from the boiling water bath, the low pH solution is allowed to cool to room temperature, and its pH is then adjusted to about pH 10 as by the addition of sodium hydroxide. The pH 10 solution is centrifuged, and the pellet formed during centrifugation is discarded while the pili-containing supernatant is retained. Adjusting the pH of the supernatant to substantial neutrality and adding a salt such as ammonium sulfate permits harvesting of the pilus subunits as a pellet following centrifugation as described above. The resulting pili subunit pellet may then be prepared into a subunit vaccine.

It is also to be understood that as used throughout this specification, the term "subunit" is not to be limited to a monomeric molecular configuration. In fact, this inventor has determined that the apparent configuration of *N. gonorrhoeae* pili subunits is hexomeric. Thus, the term "subunit" is meant to encompass oligomers as well as monomers.

More specific details of the method of this invention will be set forth in the examples presented hereinafter. The invention accordingly comprises the several steps and the relation of one or more of such steps with respect to each of the others which will be exemplified in the method hereinafter disclosed, and the scope of the invention will be indicated in the claim.

DETAILED DESCRIPTION

The present invention relates to a method for obtaining bacterium pili subunits directly from the bacteria in a liquid suspension phase. The method of this invention, with slight modification as set forth in greater detail hereinafter, has been demonstrated to be suitable for use in obtaining pili subunits from a broad variety of piliated pathogenic bacteria. Adjustments to method parameters involving pH adjustment of serial liquid suspensions are made dependent upon the bacterium from which the pili subunits are being obtained. The pili subunits, or pilin, obtained in accord with the method of this invention are then utilized to prepare vaccines exhibiting efficacy against different bacterial strains. The subunit vaccines per se are prepared in accord with normal methodology, and consist essentially of a normal saline, or buffer, solution including the pili subunits and an appropriate adjuvant. The method of this invention is particularly characterized by its steps whereby pili subunits may be obtained directly from the bacteria in a relatively simple and certainly economical manner; no detergents are utilized in obtaining the pili subunits; and, unlike intact pili preparations, the pili subunits can be sterilized by filtration. This is especially important with regard to commercial preparation of subunits and subunit vaccines.

The following examples, then, are set forth in order to describe more fully the method of the present invention.

EXAMPLE I

This example sets forth a preferred method for obtaining *E. coli* type 1 pili subunits. The F-W1-3 substrain of *E. Coli* K-12 was used exclusively. The bacteria were grown in Lennox broth consisting of 10 g of sodium chloride, 1 g of dextrose monohydrate, 10 g of tryptone (Difco Laboratories, Detroit, Mich.), and 5 g of yeast extract (Difco), made up to 1 liter with distilled water. The bacteria were harvested at mid- to late-log phase by centrifugation.

The bacteria, harvested by entrifugation from 3 liters of medium were suspended in 100 ml of TES buffer at about pH 7. The buffered bacteria solution/suspension was then adjusted to about pH 1.8 by the addition of hydrogen chloride. The resulting pH 1.8 material was then immersed in a boiling water bath for about five minutes, removed from the bath, and allowed to cool to room temperature.

Having cooled to room temperature, the solution was then adjusted to about pH 6-10 by the addition of sodium hydroxide. Centrifugation of the pH 6-10 solution resulted in the formation of a pellet which was discarded, and the pilus subunit-containing supernatant was retained.

The subunit-containing supernatant was then adjusted to about neutrality (pH 7). This final liquid phase was then concentrated to yield *E. coli* type 1 pili subunits from which a vaccine was prepared. The vaccine was prepared according to standard methodology and consisted essentially of normal saline solution, pili subunits and an appropriate adjuvant for the patient/animal to which the vaccine will be administered. Because of the relatively small size of the pili subunits, sterilization was accomplished by using a filter having a pore size of about 0.22 microns. Concentration may be accomplished by centrifugation, dialysis, the use of a desalting column, addition of a salt such as ammonium sulfate, or combinations of the above. Thus, the term "concentration" does include adjusting the pH to substantial neutrality.

EXAMPLE II

The method of Example I was repeated, but concentration of the pili subunits was accomplished by dialyzing the final liquid phase against a neutral pH buffer.

EXAMPLE III

The method of Example I was repeated, but concentration of the pili subunits was accomplished by utilizing a desalting column to remove high pH buffer.

EXAMPLE IV

This example sets forth a preferred method for obtaining *Neisseria gonorrhoeae* pili subunits. The *N. gonorrhoeae* bacteria were grown according to standard procedures and were harvested into a TES buffer solution at about pH 7. The pH of the bacteria solution/suspension was then raised to about pH 9-11, and preferably about pH 10.25-10.5, by the addition of ethanolamine buffer. This increased pH phase was then vortexed lightly to break the intact pili from the bacteria.

Following agitation, the increased pH phase was centrifuged, and the resulting pellet was discarded. The intact pili remained in the supernatant. Next, the pH of the pili-containing supernatant was raised to above pH 11.25 resulting in disruption of the intact pili into pili subunits, or pilin. Concentration yielded a quantity of pili subunit material suitable for preparing a *N. gonorrhoeae* pili subunit vaccine. The vaccine was prepared as set forth in Example I, and was sterilized by filtration as previously described.

EXAMPLE V

The method of Example IV was repeated, and concentration of the pili subunits was accomplished by dialyzing the final liquid phase against a neutral pH buffer.

EXAMPLE VI

The method of Example IV was repeated, and concentration of the pili subunits was accomplished by utilizing a desalting column to remove high pH buffer.

EXAMPLE VII

The method of Example V was repeated, but *Moraxella bovis* bacteria were utilized as the starting material. Thus, pili subunits of *M. bovis* were obtained and used to prepare a vaccine against infectious bovine keratoconjunctivitis.

In addition to the examples set forth above, additional laboratory experimentation and applied theory suggests that pili subunits may be obtained from *Neisseria meningitidis* and from *Pseudomonas aeruginosa* in accord with the methods of Examples IV, V or VI. Corresponding pili subunit vaccines may be similarly prepared. In similar fashion it is believed that pili subunits and the corresponding pili subunit vaccines may be obtained for other members of the Moraxella specie in accord with the method of Example VII. Finally, the methods of Examples I, II and III all appear to be suitable for obtaining pili subunits and corresponding pili subunit vaccines for Salmonella specie and Shigella specie.

It will thus be seen that the objects set forth above, among those made apparent from the preceding description, are efficiently attained, and since certain changes may be made in carrying out the above method without departing from the scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described, what is claimed is:

1. A method for obtaining bacterium pili subunits suitable for use in preparing a vaccine, said method comprising the steps of:
   a. harvesting the bacteria from their growth medium in a buffer solution of substantially neutral pH;
   b. adjusting the pH of the bacterial solution to about pH 9–11;
   c. agitating the pH 9–11 bacterial solution to disrupt the pili;
   d. centrifuging the pili-containing solution;
   e. discarding the pellet formed during centrifugation step d;
   f. adjusting the pH of the pili-containing supernatant retained from step e to above about pH 11.25 to obtain a pili subunit-containing solution;
   g. adjusting the pH of the subunit-containing solution to substantial neutrality; and
   h. adjusting the concentration of the pili subunit-containing material from step g to obtain the pili subunits suitable for use in preparing a vaccine.

2. A method as in claim 1 wherein the bacteria are harvested in a buffer solution at pH 6–8.

3. A method as in claim 2 wherein the bacteria are harvested in a buffer solution at about pH 7.

4. A method as in claim 1 wherein the bacteria are selected from the group consisting of *Neisseria gonorrhoeae, Neisseria meningitidis,* and Moraxella specie.

5. A method as in claim 4 wherein the bacteria are *N. gonorrhoeae.*

6. A method as in claim 5 wherein the bacteria are harvested in a buffer solution at about pH 7.

7. A method as in claim 5 wherein the bacteria solution is adjusted to about pH 10.25–10.5 at step b.

8. A method as in claim 1 wherein said final pH adjustment is accomplished by adding a salt to the pili subunit-containing solution.

9. A method as in claim 8 wherein said salt comprises ammonium sulfate.

10. A method as in claim 1 wherein said final pH adjustment is accomplished by dialyzing the pili subunit-containing solution against a neutral pH buffer solution.

11. A method as in claim 1 wherein said final pH adjustment is accomplished by using a desalting column to remove high pH buffer added in adjusting step f.

12. A method as in claim 1 further comprising the step of sterilizing the pili subunits by filtration.

13. A method for obtaining bacterium pili subunits suitable for use in preparing a vaccine, said method comprising the steps of;
   a. harvesting bacterials selected from the group consisting of *Escherichia coli, Salmonella* specie, and *Shigella* specie from their growth medium in a buffer solution of substantially neutral pH;
   b. adjusting the pH of the bacterial solution to below about pH 2;
   c. placing the lowered pH bacterial solution in a boiling water bath for about 5 minutes;
   d. removing the heated solution from the bath and allowing it to cool to room temperature;
   e. adjusting the pH of the cooled solution from step d to about pH 6–10;
   f. centrifuging the solution of step e;
   g. discarding the pellet formed during centrifugation step f;
   h. adjusting the pH of the subunit-containing supernatant retained from step g to substantial neutrality; and
   i. adjusting the concentration of the pili subunit-containing material from step h to obtain the pili subunits suitable for use in preparing a vaccine.

14. A method as in claim 13 wherein the bacteria are *E. Coli.*

15. A method as in claim 14 wherein the bacteria are harvested in a buffer solution at about pH 6–8.

16. A method as in claim 14 wherein the pH of the bacterial solution is adjusted by adding hydrogen chloride.

17. A method as in claim 16 wherein the pH is adjusted to about pH 1.8.

18. A method as in claim 14 wherein the pH of the cooled solution is adjusted by adding sodium hydroxide.

19. A method as in claim 14 wherein said final pH adjustment of the pili subunits is accomplished by adding a salt to the supernatant retained from step g.

20. A method as in claim 14 wherein said final pH adjustment of the pili subunits is accomplished by dialyzing the supernatant retained from step g against a neutral pH buffer solution.

21. A method as in claim 14 wherein said final pH adjustment of the pili subunits is accomplished by using a desalting column to remove high pH buffer added in adjusting step e.

22. A method as in claim 13 further comprising the step of sterilizing the pili subunits by filtration.

* * * * *